(12) United States Patent
Pham et al.

(10) Patent No.: US 6,919,303 B2
(45) Date of Patent: Jul. 19, 2005

(54) PROCESS FOR LOWERING LEVEL OF SALT REQUIRED FOR DILUTION THICKENING

(75) Inventors: Quynh Pham, Murray Hill, NJ (US); Rajesh Patel, Lyndhurst, NJ (US); Michael Massaro, Monroe, CT (US); Joann Mathias, Brooklyn Heights, NY (US)

(73) Assignee: Unilever Home & Personal Care, division of Conopco, Inc., Greenwich, CT (US)

( * ) Notice: Subject to any disclaimer, the term of this patent is extended or adjusted under 35 U.S.C. 154(b) by 28 days.

(21) Appl. No.: 10/643,229

(22) Filed: Aug. 18, 2003

(65) Prior Publication Data

US 2005/0043193 A1 Feb. 24, 2005

(51) Int. Cl.$^7$ .................................................. A61K 7/00
(52) U.S. Cl. ................. 510/130; 510/158; 510/159; 510/471; 510/473; 510/477; 510/479; 510/425
(58) Field of Search .................................. 510/425, 471, 510/473, 477, 479, 130, 156, 158, 136, 421, 424, 505

(56) References Cited

U.S. PATENT DOCUMENTS 5,393,450 A * 2/1995 Shana'a ...................... 510/158
6,427,177 B1 7/2002 Chang

FOREIGN PATENT DOCUMENTS

| CA | 2211313 | 2/1998 |
| WO | 94/16680 | 8/1994 |
| WO | 94/23695 | 10/1994 |

* cited by examiner

*Primary Examiner*—Necholus Ogden
(74) *Attorney, Agent, or Firm*—Ronald A. Koatz

(57) ABSTRACT

The invention relates to a process for making single phase dilution thickening compositions comprising electrolyte. By adding defined associative thickener to said compositions applicants have found one can lower level of salt/electrolyte required to obtain dilution thickening effect.

2 Claims, 6 Drawing Sheets

(a)

(b)

Effects of MgSO$_4$ and NaCl on formulations containing 16% SLES, 3% CAPB, 0% Rewoderm LIS75, and 0% PEG400.

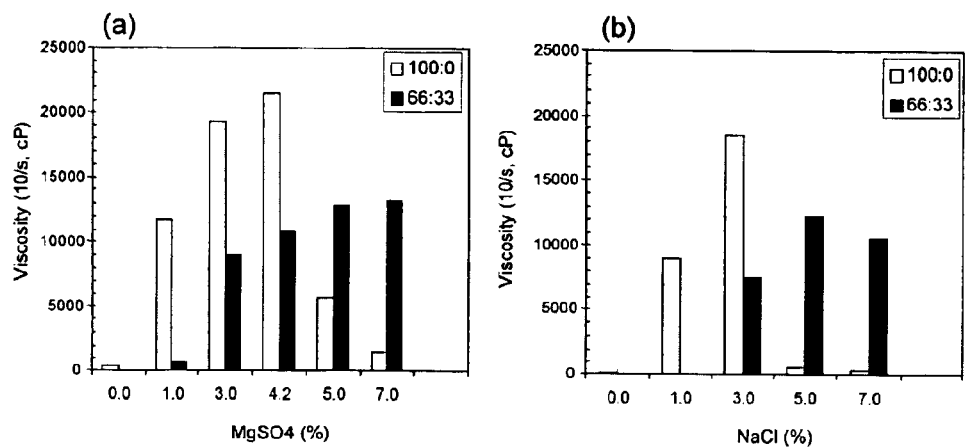
*Figure 1:* Effects of $MgSO_4$ and NaCl on formulations containing 16% SLES, 3% CAPB, 0% Rewoderm LIS75, and 0% PEG400.

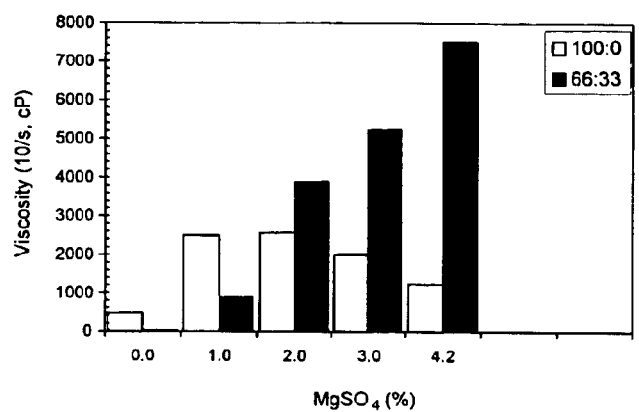
Figure 2: Effect of $MgSO_4$ concentration neat and diluted samples of monophasic and biphasic formulations (16% SLES, 3% CAPB, 4% Rewoderm LIS 75,11% PEG400). $MgSO_4$ concentration labels are of the neat samples.

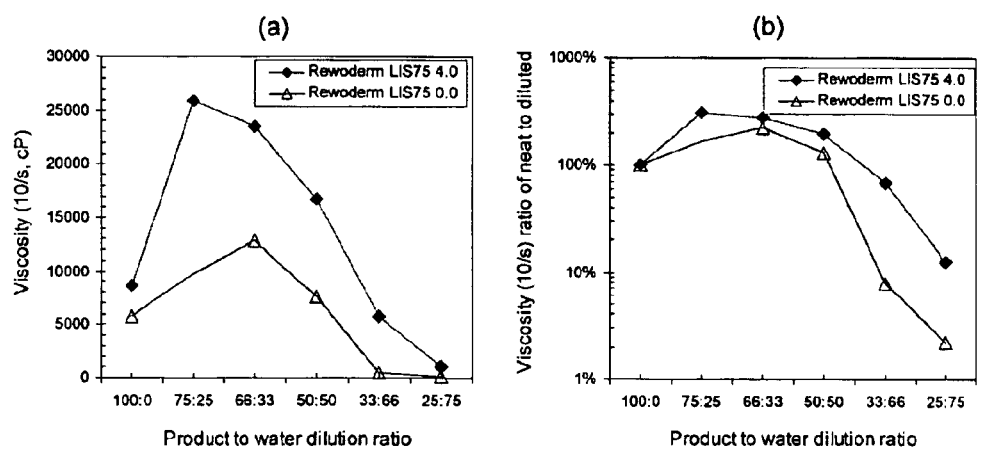
Figure 3: Dilution thickening effects on formulations of (16% SLES, 3% CAPB, 0% PEG400, 5% MgSO$_4$) with and without 4% Rewoderm LIS75; (a) absolute viscosities as function of dilution ratio, (b) percent ratios of diluted to initial viscosities.

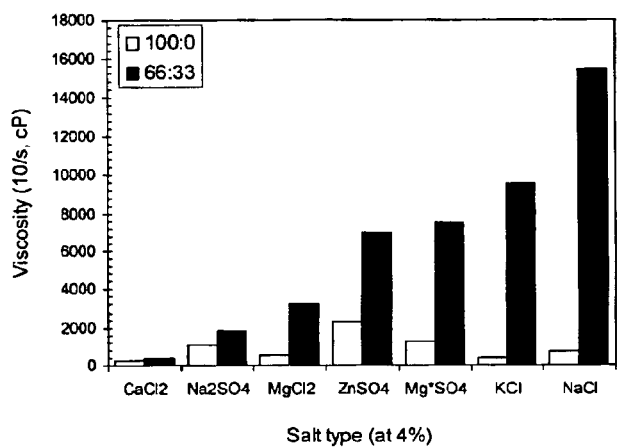
Figure 4: Effect of salts on neat and diluted samples of formulations containing 16% SLES, 3% CAPB, 4% Rewoderm LIS 75, 11% PEG400. Salt concentration was fixed at 4%. All samples were monophasic.

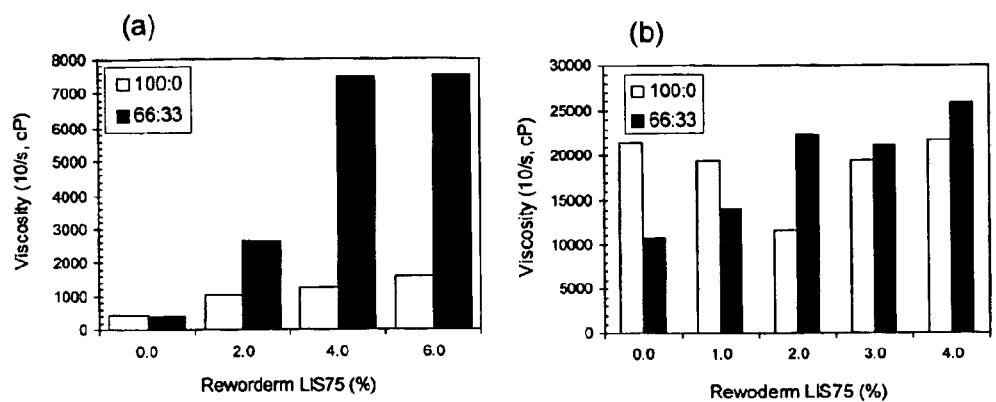
Figure 5: Effect of Rewoderm LIS75 concentration on formulations with 16%SLES, and 3% CAPB; samples in plot (a) also contains 4.2% MgSO$_4$ and 11% PEG400, samples in (b) contains 4% MgSO$_4$ and 0% PEG400.

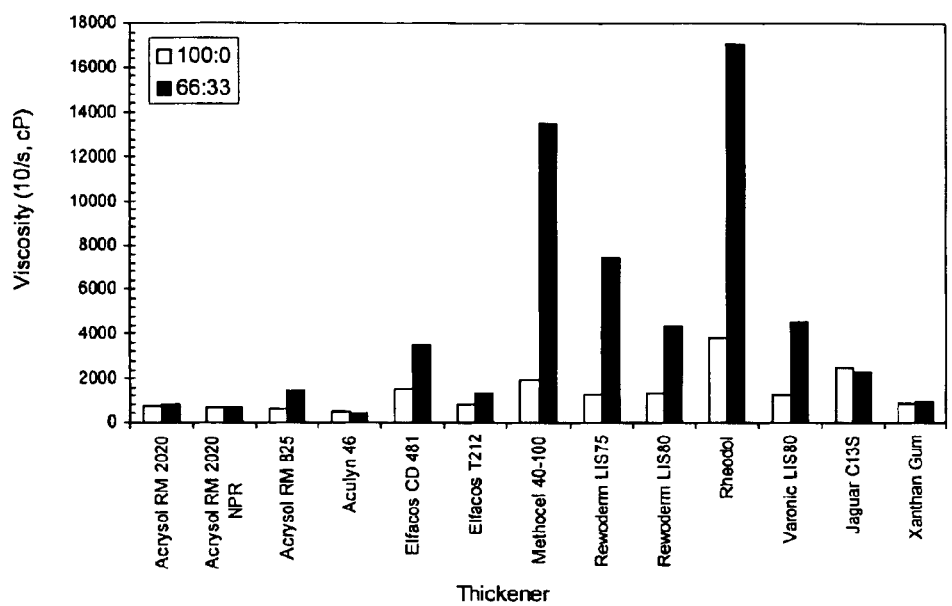
Figure 6: Effect of thicker types or formulations with 16% SLES, 3% CAPB, 11% PEG400, and 4.2% $MgSO_4$. All thickeners listed were soluble in this surfactant salt composition. Thickener concentrations are fixed 4% except for Jaguar C13S and xanthan gum, which were reduced to 1% due to the high viscosity of the neat product.

PROCESS FOR LOWERING LEVEL OF SALT REQUIRED FOR DILUTION THICKENING

FIELD OF THE INVENTION

The present invention relates to liquid cleansing compositions which have a viscosity which allows them to readily pour from a bottle or container, but which viscosity increases during dilution/rinsing. In particular, the invention relates to a process for lowering level of salt required for producing dilution thickening effect using associative thickeners. Compositions comprising such thickeners are characterized by a cohesive "film" forming on treated skin which, in turn, deters rinsability, as measured by a rinse retention test, and allows for enhanced ease of spreading.

BACKGROUND OF THE INVENTION

The use of salts to thicken surfactant systems and enhance viscosity is not new (see Canadian Patent No. 2,211,313). Typically, a so-called peak viscosity is achieved when salt is first added, and further addition of salt leads to viscosity reduction (this is known as oversalting). When the composition is diluted, the "oversalted" composition then increases in viscosity once more in a process referred to as "dilution thickening."

Dilution thickened compositions typically will form a film on the skin which lacks cohesion. As such the film will dissolve and quickly wash away. As such, the dilution thickening compositions are generally perceived as readily rinsable and difficult to spread.

Unexpectedly, applicants have found that when, in addition to the level of salt required to form "oversalted" compositions, an associative thickener (e.g., hydrophobically modified PEG such as PEG-200 glyceryl tallowate, such as Rewoderm® LIS75 or PEG-7 glyceryl cocoate) is also used, the film on the skin is far more cohesive, thereby leading to reduced rinsability and greater spread on the cleansed surface. This in turn permits consumer to use less product and offers sensory benefit, both with and without use of additional applicator/implement during use.

In addition, applicants have found use of associative thickener lessens the amount of salt needed to induce dilution thickening.

WO 94/16680 to Unilever discloses aqueous dilution thickening, concentrated liquids comprising 20 to 60% surfactant other than soap or primary alcohol sulphate. The compositions are said to form a low viscosity, lamellar phase in the undiluted product and, when diluted, to form into a more viscous rod or hexagonal phase.

There appears to be no disclosure of the hydrophobically modified associative thickeners of the invention or of the effect of such thickeners in lowering level of salt required for dilution thickening.

Canadian Patent No. 2,211,313 also discloses compositions which have been oversalted and increase in viscosity upon dilution.

While there is a broad list of thickeners disclosed (page 9, third paragraph), there is no disclosure of the specific use of hydrophobically modified associative polymer or of its effect in lowering salt level required to see dilution thickening effect.

U.S. Pat. No. 6,427,177 to Williams et al. entitled "A Separating Multiphase Personal Wash Compositions in a Transparent or Translucent Package" discloses a biphasic or multiphasic liquid in which, in one of the phases, can be found high levels of electrolyte and an associate thickener.

The compositions of the reference are multiphasic before dilution and may or may not be monophasic upon dilution. They also require that much higher levels of electrolyte be used in order to form the biphasic in the first place. By contrast, the compositions of the subject invention are single phase compositions prior to dilution.

There is also no disclosure of a process for lowering level of salt required to obtain dilution thickening effect using specific associative thickeners.

BRIEF DESCRIPTION OF INVENTION

Applicants have now found a single phase, isotropic, undiluted compositions comprising:

(1) 5 to 30% by wt. of a surfactant or surfactants for cleansing the skin;
(2) an amount of electrolyte from about 2% to an upper level defining a boundary between monophasic and multiphasic, said upper boundary preferably being less than about 9%, more preferably 6% or less;
(3) 0.5 to 7%, preferably 1 to 5% by wt. associative thickener;
(4) 0 to 15% by wt., preferably 1 to 10% by wt. hydrotroping compound; and
(5) 45 to 95% by wt. water, wherein, said composition has viscosity upon dilution, which is greater than viscosity prior to dilution;
wherein said composition has rinse retention of greater than 30% after 10 minutes as measured by tested sample retained on a test slide as function of rinsing time; and
wherein, upon dilution, said composition remains in a single phase.

Isotropic liquids comprising a combination of electrolyte salt and hydrophobically modified associative thickener have been found to pour readily out of containers; thicken upon rinsing; and, presumably because of a cohesive film formed on the skin (applicants do not wish to be bound by theory in this regard), to both spread readily and to stay on the skin readily, as measured in a rinse retention test.

In addition, applicants have found a process to lower level required for dilution thickening using associative thickeners of the invention.

BRIEF DESCRIPTION OF FIGURES

FIG. 1 describes the effects of varying levels of salt on dilution thickening compositions without the associative polymer of the invention. As seen, dilution thickening on the monophasic composition begins at about 5% salt (by contrast, when associative polymer of the invention is used, point of which dilution thickening occurs shifts left or downwards, i.e., less salt is needed).

FIG. 2 describes effect of $MgSO_4$ salt on the clear, monophasic compositions of the invention with associative polymer. As seen, the polymer shifts dilution thickening phenomena to 2% salt in single phase liquids (by contrast, compositions of Williams et al., for example, are biphasic and will presumably have higher levels of salt).

FIG. 3 describes the effect of associative polymer on absolute viscosity as a function of dilution ratio (FIG. (a)).

FIG. 4 describes the effect of various salts (all at 4% concentration) on dilution thickening. As seen, some salts are more effective than others.

FIG. 5 describes the effect of associative thickener on dilution thickening. FIG. 5(a) shows effect with PEG and 5(b) with no PEG.

FIG. 6 summarizes thickening effect of various associative thickeners.

DETAILED DESCRIPTION OF THE INVENTION

Dilution thickening is generally defined as any diluted sample having a viscosity greater than that of a neat product (100:0 product to water). Generally, using relatively large amounts of salt (e.g., >5%) the effect is achieved. This can be seen, for example, in FIGS. 1(a) and 1(b) where formulations comprising surfactants and varying levels of $MgSO_4$ or NaCl show dilution thickening behavior (at 66:33 dilution) beginning at 5% salt level.

Previous work (for example in U.S. Pat. No. 6,427,177 to Williams) has been done with so-called biphasic liquids. In that work, phase separation was seen as a function of both salt content and content of polyalkylene glycol. At high levels of polyalkylene glycol (e.g., 11%), compositions were found to be clear, isotropic, one phase solutions at salt levels of under or about 8%.

In the present invention it was also found that, when 8% or more salt was used in the undiluted top layer of a biphasic liquid with no polyalkylene glycol and comprising associative polymer, the top phase was cloudy, hazy and opalescent. Since it is desired to have initially clear liquids, the compositions of the invention generally will comprise less than 9% salt, preferably less than 6% salt. It should be noted that the only real upper limit is that there be less electrolyte than the amount which would induce formation of biphasic since one of the ways in which compositions of the invention distinguish over Williams is that they are not biphasic.

Indeed, it is one of the advantages or improvements of the invention over the prior art that, when using monophasic liquid compositions it is possible to shift the point at which the dilution thickening effect of salt is seen from at least 5% (see FIGS. 1(a) and 1(b)) to levels of as low as 2%. This can be seen, for example in FIG. 2 where, when associative polymer and PEG are used, thickening begins as low as at 2% salt.

Another benefit of the compositions of the invention is that, relative to compositions without thickener, the thickener imparts higher viscosity throughout the dilution process and maintains the effect of the dilution action. This is seen in FIG. 3.

That is, for example, without thickener at 5% $MgSO_4$, the absolute viscosity drops sharply after about a 50:50 dilution ratio. With 4% Rewoderm LIS75 at the same salt concentration, dilution thickening is observed up to 40:60 dilution, and the drop off is more gradual. The overall viscosities of the samples with thickener were also higher. Plotted as percent ratios between the initial and diluted viscosities of the samples, FIG. 3, the thickener gave more dilution thickening effect, i.e. the viscosity ratios are higher with thickener than without. Moreover, after the drop off in viscosities, diluted samples with thickener still maintained at least 10% of their initial viscosity at 25:75 dilution; without Rewoderm LIS75, this viscosity ratio is only 1% at this dilution.

Finally, another advantage over the art is the "cohesivity" supplied by the thickener. This is manifested as larger retention of the dilution thickened shower gel on the skin and other surfaces (see rinse retention test and results in examples).

More specifically, the present invention relates to novel, single phase, isotropic, liquid composition comprising:

(1) 5% to 30%, preferably 8% to 25% by. wt. surfactant or surfactants;

(2) from about 2% electrolyte to an upper level amount which is both below about 9% and not high enough to induce formation of biphasic, preferably, this is below about 8%, more preferably below about 6% by wt. electrolyte;

(3) 0.5% to 7%, preferably 1% to 5% by wt. hydrophobically modified, preferably although not necessarily nonionic associative thickener;

(4) 0% to 15%, preferably 1% to 10% by wt. hydrotroping compound; and (5) 45% to 95% by wt. water, wherein, said composition has viscosity upon dilution, which is greater than viscosity prior to dilution;

wherein said composition has rinse retention of greater than 30% after 10 minutes as measured by a sample retained on a test slide as a function of rinsing time; and wherein, upon dilution, said composition remains in a single phase.

The invention further relates to a process for lowering level of salt required to obtain dilution thickening, when using monophasic liquid composition, by utilizing associative thickener.

The compositions of the invention should contain 5% to 30% by wt. total composition of one or more anionic, amphoteric or nonionic surfactant.

Anionic, amphoteric, nonionic surfactant or mixtures thereof may be used according to the present invention. The anionic surfactants which are suitable for use according to the present invention include alkyl sulphates, ether alkylsulphates, alpha olefin sulphonate, sulphosuccinates, soaps, N-acyl sarcosinates, N-acyl glutamates, N-acyl polypeptide condensates, acyl isethionates, N-acyl methyl taurates, alkyl benzene sulphonates, alcohol sulphates and phosphate esters among other.

Preferred examples of anionic surfactants are sodium lauryl sulphate, triethanolamine lauryl sulphate, ammonium lauryl sulphate, ammonium ether lauryl sulphate, sodium ether lauryl sulphate, soap, sodium xylene sulphate, sodium sulphosuccinate, sodium olefin, $C_{14}$–$C_{16}$ sulphonate, MEA disodium cocoamido sulphosuccinate, sodium benzene sulphonate, sodium cocyl isethionate amongst others.

The anionic surfactant preferably includes an ether alkyl sulphate of general formula (I):

$$R\text{—}O\text{—}(CH_2\text{—}CH_2O)_n SO_3^-  \qquad (I)$$

wherein

N is 1 to 5 and R is $C_8$–$C_{18}$, preferably $C_{12}$.

The amphoteric surfactants which may be used according to the present invention include alkyl glycinates and propionates, carboxy glycinates, alkyl betaines, alkyl imidazolines sulpho betaines, alkyl polyamino carboxylates, alkyl-amino/imonopropionates and poly ampho carboxyglycinates, amongst others. Preferred examples of amphoteric surfactants are coco-amido-propyl-betaine, sodium-coco-amphocarboxy-glycinate, coco-amido, sulpho betaine, coco-ethoxylated MEA, and alkyl-dimethyl-betaine amongst others.

The preferred amphoteric surfactants are alkyl-amido-propyl betaines of general formula (II):

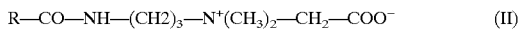

$$R\text{—}CO\text{—}NH\text{—}(CH2)_3\text{—}N^+(CH_3)_2\text{—}CH_2\text{—}COO^- \qquad (II)$$

wherein R has the same meaning as in Formula (I).

It is especially preferred that the alkyl-amido propyl-betaine is coco-amido-propyl-betaine wherein R is a chain of coco fatty acid with 12 carbon atoms.

The nonionic surfactants which may be used according to the present invention include the polyalkoxylated fatty alcohols and acids and their esters, alkanolamides, polyalkoxylated and ethoxylated alkanolamides, glycosides and alkyl-polyglycosides, and long chain ethoxylated amines, alkyl-amines, amine-oxides, polysorbate, nonoxinols, and polyoximefts amongst other.

Preferred examples of nonionic surfactants include polysorbate 20, nonoxinon-12, polyethylene-24 lauric acid, coco MEA, and cetyl isooctanoate, amongst others.

A preferred nonionic surfactant is the amino oxides of general formula (III):

$$R^1R^2R^3\text{—}NO$$

wherein $R^1$ is a $C_{2\text{-}20}$ alkyl group and $R^2$ and $R^3$ are $C_{1\text{-}4}$ chain alkyls.

The typical concentration of surfactant in the compositions of the present invention lies between 5%, 30% by weight based upon the total weight of the composition, preferably between 8% and 25% by weight, most preferably between 10% and 20% by weight.

Among the electrolytes (organic and inorganic) which may be used in accordance with the invention are halides of alkaline metals, alkaline earth metals, ammonium and other metals, such as aluminum and zinc; sulphates and phosphates of alkaline metals, alkaline earth metals, ammonium and other metals such as aluminum and zinc; MEA and DEA salts, and alkaline metal silicates, among other.

Preferred examples of electrolytes used according to the present invention are: sodium chloride, potassium chloride, sodium sulphate, potassium sulphate, magnesium chloride, magnesium sulphate, zinc sulphate, ammonium chloride and MEA chloride among others.

As indicated above, in order to ensure that there is dilution thickening, there is needed at least about 2% salt/electrolyte. However, to ensure, prior to dilution, the composition is single phase, the salt/electrolyte should be used in amount below the amount which would cause it to become biphasic. This depends on the salt and generally would be expected to be below about 9% (again depending on whether inclusion will precipitate formation of biphasic), preferably below about 6%.

As seen in the examples, the level of salt generally will be about 2 to about 6% although, as noted, the upper limit is defined in reality only as that amount which will cause formation of multiphasic from the monophasic state. As also seen in the examples (FIG. 4), particularly preferred dilution thickening salts include potassium and sodium chloride. Specifically, FIG. 4 shows the viscosities of the neat and diluted samples containing various salts. At 4% salt, the neat samples containing $ZnSO_4$, $MgSO_4$, and $Na_2SO_4$ appeared most viscous. $MgCl_2$, KCl, and NaCl have little thickening effect on the initial composition of SLES, CAPB, PEG400, and Rewoderm LIS75. However, upon dilution, the monovalence salts KCl and NaCl produced tremendous increases in viscosities to form very viscous gels. $ZnSO_4$ and $MgSO_4$ were also effective at producing large dilution thickening.

Dilution thickening was observed for all soluble salts at 4%. Comparatively, at 66:33 dilution, as much as 20 times increase in the viscosity was observed with NaCl and KCl, 3 to 6 times for $MgCl_2$, $MgSO_4$, and $ZnSO_4$, and minor increase was observed with $Na_2SO_4$. Effect with $CaCl_2$ was not certain due to its solubility at 4% in the formulation; $CaCl_2$ appeared insoluble and precipitated.

Associative Thickener 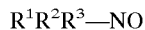

As seen from FIG. 5(a), when various levels of an associative thickener (e.g., Rewoderm® LIS75, tradename of PEG-200 glyceryl tallowate) were used (i.e., in composition having 16% anionic, 3% betaine, 11% PEG 400 and 4.2 $MgSO_4$), there was modest and linear increase in neat sample single viscosity. Samples diluted to 66:33 had increasing viscosities from 0 to 4% and plateaued at 4 to 6%. Dilution thickening was observed only when at least some Rewoderm was present (i.e., not at 0.0%).

As also seen in FIG. 5(b), when PEG was not present there was no viscosity increase in diluted samples at 0 and 1%, suggesting that at least about 2% thickener (e.g., Rewoderm) may be needed in the absence of PEG.

In general, at least 0.5% thickener is needed, preferably at least 2%.

The associative thickeners (preferably, but not necessarily, nonionic thickeners) are essentially hydrophobically (e.g., tallowate) modified hydrophilic (e.g., water soluble polyalkylene glycol) backbone. While not wishing to be bound by theory, the mechanism for viscosity enhancement is believed due to interactions or associations of the hydrophobic groups with each other and/or with hydrophobic components of the formulations. Also, because the thickening mechanism is independent of charge, the polymers are preferably nonionic and can be used in high salt environments. Examples of associative thickeners similar to. Rewoderm® LIS75 are Rheodol® (tristearate modified PEG) and Elfacos® T212 (carbamic acid diester of the polyoxypropylene, polyoxyethylene ether of the fatty alcohols derived from palm kernel oil). Other associative thickeners include ethylene glycol ether of ethylene cellulose (hydrooxyethyl ethylcellulose) such as Elfacos® CD481; or ethyl glycol ether of methyl cellulose, such as Methocel® 40-10.

A number of other standard thickeners in personal cleansers were also tested. Several such as Carbopol® ETD2020, Klucel® HF NF, and Aculyn® 22 were salt intolerant and precipitated in the high salt formulations. Jaguar C13S and xanthan gum were compatible but due to their high molecular weight and the subsequent high viscosities generated, they were tested at only 1% or less. FIG. 6 summarizes the results for different polymers. In the neat samples, the polymers have varying thickening efficiency. Rheodol, Jaguar, and Methocel were highly effective at thickening the neat samples. Rewoderm® LIS80 and Varonic® LIS80 have similar structures as and behaved much like Rewoderm® LIS75. The Table below provides names, definitions and structures of various polymers which may be used although it is to be understood that these are for illustrative purposes and many other polymers may have been cited.

synergistic advantages. First, it shifts lower the level of salt required before the effect can occur (e.g., to 2% rather than 5%). Second, rheologically, it imparts higher viscosity throughout the dilution process and maintains the effect of higher dilution ratio (FIG. 3). Finally, as noted in examples, the combination leads to enhanced rinse retention.

Optionals

In addition to the ingredients noted above, the compositions of the invention may contain a variety of optional ingredients such as set forth below:

| Name | Sources | Definition | Structure |
|---|---|---|---|
| PEG-200 glyceryl tallowate | Rewoderm LIS75 | Polyethylene glycol ether of tallow glyceride that conforms to the structure where RCO represents the fatty acids derived from tallow and n has an average value of 200; the R group represents the hydrophobe | $RC(=O)-OCH_2CHCH_2(OCH_2CH_2)_nOH$ with $OH$ on middle carbon |
| PEG-200 hydrogenated glyceryl palmate | Rewoderm LIS80 | Polyethylene glycol derivative of hydrogenated palm glyceride. It has an average of 200 moles of ethylene oxide. | |
| PEG-7 glyceryl cocoate | mixed in with Rewoderm LIS75 and LIS80 | Polyethylene glycol ether of glyceryl cocoate that conforms generally to the structure where RCO— represents the fatty acids derived from coconut oil and n has an average value of 7. | $RC(=O)-OCH_2CHCH_2(OCH_2CH_2)_nOH$ with $OH$ on middle carbon |
| PEG-160 sorbitan triisostearate | Rheodol TW-IS399C | Triester of isostearic acid and a polyethylene glycol ether of sorbitol with an average of 160 moles of ethylene oxide. | |
| PPG-14 palmeth-60 hexyl dicarbamate | Elfacos T212 | Carbamic acid diester of the polyoxypropylene, polyoxyethylene ether of the fatty alcohols derived from palm kernel oil. It has the structure where x is 60 (average), y is 14 (average), and R represents the fatty alcohols derived from palm kernel oil. | $[R(OCHCH_2)_y(OCH_2CH_2)_kO-C(=O)-NH(CH_2)_6-]_2$ with $CH_3$ branch |
| Hydroxyethyl Ethylcellulose | Elfacos CD481 | Ethylene glycol ether of ethyl cellulose | |
| Hydroxypropyl methylcellulose | Methocel 40-100 | Ethylene glycol ether of methyl cellulose | |

As seen in FIG. 6, at 66:33 dilution, the polymers that clearly exhibited dilution thickening behavior were Rewoderm LIS75 and LIS80, Elfacos T212 and CD481, Rheodol, Varonic LIS80, and Methocel 40-100. The Acrysol RM825 appeared to maintain or even slightly increase viscosity. The non-hydrophobically modified polymers (Jaguar C13S and xanthan gum) did not thicken upon dilution. It can be seen that the associative nature of the polymers aids in the dilution thickening phenomenon.

Hydrotrope

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase and hence increasing its apparent concentration.

Combination Effect of Salt and Associative Thickener

As noted above, while salt is required for dilution thickening, use of associative polymer with salt provides The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, enzyme and $\alpha$- or $\beta$-hydroxy acid either alone or entrapped in an oily benefit agent.

The benefit agent may be found in either the upper or the lower layer depending on its solubility and partition coefficient, for example, oil may partition into the upper layer while more water soluble agents (e.g., $\alpha$-hydroxyacids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, EGMS (ethylene glycol monostrearate) or styrene/acrylate copolymers.

The compositions may further comprise antimicrobials such as 2-hydroxy 4,2'4'trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330-Polyquaternium 39; and Jaguar® type conditioners.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

In addition to composition elements, it is critical that compositions of the invention meet the following requirements.

First, they are dilution thickening, by which is meant that the composition, upon dilution, has viscosity greater than that prior to dilution.

Second, they must have rinse retention defined by retention of greater than 30% by weight, after 10 minutes of soaking/rinsing in water as measured by amount of sample retained on a test slide as function of rinsing time.

Third, the composition must be single phase before dilution.

Methodology

| Raw Materials | Trade Name |
|---|---|
| Sodium Laureth Ether Sulfate (69% actives) (SLES) | Genapol LRO SLES |
| Coco Amido Propyl Betaine (30% to 39% actives) (CAPB) | Dehyton K CAPB |
| Salts (MgSO$_4$, NaCl, KCl, MgCl$_2$, CaCl$_2$, Na$_2$SO$_4$, ZnSO$_4$) | |
| Poly(ethylene glycol) (400 EO's) | PEG400 |

Formulation Preparation

A 75% concentrated surfactant base was first prepared with SLES, CAPB, and perfume. The 25% hole or deficit was reserved for later addition of water, thickener and salt. The final composition contained 16% SLES, 3% CAPB and 1% perfume.

Base Formulation Preparation

Preparation was as follows:
1) Using jacketed beaker and water bath, water was heated to 65° C. and mixing started with overhead stirrer.
2) SLES was added to water.
3) Formulation was checked for clumps which were broken as required.
4) Temperature was lowered and CAPB was added.
5) Composition was cooled to room temperature and perfume was added.

Full Formulation Preparation

Subsequent addition of thickener, polyethylene glycol, and salt to the concentrated base above was done at room temperature using an overhead mixer until homogenized. For example, to prepare formulation with 16% SLES, 3% CAPB, 1% perfume and 1% thickener, 1 g of thickener (assuming 100% active) and 24 g of water was added to 75 g of above base. Likewise to prepare formulation with 16% SLES, 3% CAPB, 1% perfume and 9% MgSO$_4$-anhydrous, 17 g MgSO$_4$—7H$_2$O and 8 g of water were added.

A typical formulation of the invention is as follows:

| Ingredient | % by wt. |
|---|---|
| Sodium lauryl ether sulfate (SLES) | 16 |
| Rewoderm LIS75 | 4 |
| Cocoamidopropyl betaine (CAPB) | 3 |
| PEG 400 | 11 |
| MgSO$_4$ | 4 |
| Perfume | 1 |
| Water | Balance |

Rheology Measurement

Rheology measurements were conducted using a controlled strain rheometer (Rheometric Scientific ARES) primarily. A Haake viscometer was used intermittently for quick checks of prototypes. All data reported here were measured using ARES rheometer with the cone and plate or Couette geometry at 25° C. The shear rate sweeps were run in logarithmic mode from 0.1 to 1000 s$^{-1}$, with 5 points per decade. Viscosities are quoted for a fixed shear rate at 10 s$^{-1}$.

For dilution data, viscosity measurements were conducted on equilibrated samples. The formulations were first mixed with deionized water at appropriate ratios by weight, using magnetic stir bars or wrist shaker, and allowed to equilibrate for 4 hours to overnight, all at room temperature. Shear sweeps were then done as described above.

EXAMPLES

Example 1

In order to show the dilution thickening effect and amount of salt normally needed to cause the effect, applicants prepared compositions s follows:

| | |
|---|---|
| SLES | 16% |
| CAPB | 3% |
| Thickener | 0% |
| PEG 400 | 0% |

Levels of salt (MgSO$_4$ and NaCl) varied from 0 to 9% and viscosities were tested both neat (100:0) and at dilution of 66:33. Results are set forth in FIGS. 1(a) and 1(b).

As discussed in the specification above, when no polymeric thickener is used, the diluted thickening effect is not seen until 5% salt is used.

By contrast, applicants tested compositions having formulation as follows:

| | |
|---|---|
| SLES | 16% |
| CAPB | 3% |
| Rewoderm (LIS75) | 4% |
| PEG 400 | 11% |

Results under varying levels of MgSO$_4$ are seen in FIG. 2. With thickener, it can be seen that level of salt to induce dilution thickening is as low as 2%. Thus, this thickener clearly induces a shift.

Example 2

In order to show difference in dilution behavior of salts with or without thickener, applicants tested the following formulation:

| | |
|---|---|
| SLES | 16% |
| CAPB | 3% |
| PEG 400 | 0% |
| MgSO4 | 5% |
| Rewoderm LIS75 | 4% or 0% |

The results are set forth in FIGS. 3a and 3b.

As can be clearly seen, rheologically the thickener imparts higher viscosity increases throughout the dilution process and maintains the effect of higher dilution. Specifically without thickener at 5% MgSO$_4$, the absolute viscosity drops sharply after about a 50:50 dilution ratio. With 4% Rewoderm LIS75 at the same salt concentration, dilution thickening is observed up to 40:60 dilution, and the drop off is more gradual. The overall viscosities of the samples with thickener were also higher. Plotted as percent ratios between the initial and diluted viscosities of the samples, FIG. 3b, the thickener gave more dilution thickening effect, i.e. the viscosity ratios are higher with thickener than without. Moreover, after the drop off in viscosities, diluted samples with thickener still maintained at least 10% of their initial viscosity at 25:75 dilution; without Rewoderm LIS75, this viscosity ratio is only 1% at this dilution.

Example 3

In order to show effect of salt concentration and type, applicants tested the following compositions:

| | |
|---|---|
| SLES | 16% |
| CAPB | 3% |
| Rewoderm LIS75 | 4% |
| PEG 400 | 11% |
| Salt (Varying) | 4% |

Results are set forth in FIG. 4.

FIG. 4 shows the viscosities of the neat and diluted samples containing various salts. At 4% salt, the neat samples containing ZnSO$_4$, MgSO$_4$, and Na$_2$SO$_4$ appeared most viscous. MgCl$_2$, KCl, and NaCl have little thickening effect on the initial composition of SLES, CAPB, PEG400, and Rewoderm LIS75. However, upon dilution, the monovalence salts KCl and NaCl produced tremendous increases in viscosities to form very viscous gels. ZnSO$_4$ and MgSO$_4$ were also effective at producing large dilution thickening.

Dilution thickening is observed for all soluble salts at 4%. Comparatively, at 66:33 dilution, as much as 20 times increase in the viscosity is observed with NaCl and KCl, 3 to 6 times for MgCl$_2$, MgSO$_4$, and ZnSO$_4$, and minor increase was observed with Na$_2$SO$_4$. Effect with CaCl$_2$ was not certain due to its solubility at 4% in the formulation; CaCl$_2$ appeared insoluble and precipitated.

Example 4

In order to show the effect of varying concentration of associative thickener, applicants tested the following compositions:

| | |
|---|---|
| SLES | 16% |
| CAPB | 3% |
| PEG | 11% or 0% |
| MgSO$_4$ | 4.0 or 4.2% |
| Rewoderm LIS75 | Varying |

Results are set forth in FIG. 5. As seen in FIG. 5(a), as the amount of thickener increases in composition without PEG, there is a modest linear increase in viscosity of the neat sample. The viscosities increase at 0% to 4% and plateau between 4% and 6%.

With 4.2% MgSO$_4$ and 11% PEG400, dilution thickening was observed only when Rewoderm LIS75 was present. Similar effect was observed in formulations without PEG400. FIG. 5(b) shows the trends for compositions with 4% MgSO4, 0% PEG400, and 0 to 4% Rewoderm LIS75. In the absence of hydrotropic PEG, the high viscosities of the neat samples come mostly from the salt (MgSO$_4$) and the thickener appeared to contribute little effect. Comparing the neat samples, 0% Rewoderm LIS75 has a viscosity of 21,500 centipoises, while those containing 1 to 4% Rewoderm LIS75 have viscosities between 11,500 and 21,700 centipoises. Method given under Rheology Measurement: ARES or Haake rheometer, shear rate of 10 s$^{-1}$, 25° C.

In the diluted samples, the viscosity increase was not observed at 0 and 1% Rewoderm LIS75. Dilution thickening was significant at 2% Rewoderm LIS75 and modest at 3 and 4% Rewoderm LIS75. This suggests that at 4% MgSO4, with and without PEG400, Rewoderm LIS75 concentration at greater than 1% is required for dilution thickening.

Example 5

In order to show dilution thickening effect of various thickener types, applicants tested the following formulations.

| | | |
|---|---|---|
| | SLES | 16% |
| | CAPB | 3% |
| | PEG 400 | 11% |
| | MgSO4 | 4.2% |
| | Thickener | 4%* |

*except Jaguar Cl3S and Xanthan gum, which were reduced to 1% due to high viscosity of the neat product.

Results were set forth in FIG. 6. As seen, in the neat samples, the polymers have varying thickening efficiency. Rheodol, Jaguar, and Methocel are highly effective at thickening the neat samples. Rewoderm LIS80 and Varonic LIS80 have similar structures as, and behaved much like, Rewoderm LIS75.

At 66:33 dilution, the polymers that clearly exhibited dilution thickening behavior were Rewoderm LIS75 and LIS80, Elfacos T212 and CD481, Rheodol, Varonic LIS80, and Methocel 40-100. The Acrysol RM825 appeared to maintain or even slightly increase viscosity. The non-hydrophobically modified polymers (Jaguar C13S and xanthan gum) did not thicken upon dilution. It appeared that the associative nature of the polymers aid in the dilution thickening phenomenon.

Example 6

Rinse Retention

The enhanced retention of the dilution thickening effect was clearly observed during a handwash with the samples. Samples containing the associative thickener of the invention formed a sticky film on skin that persisted for a long time during the rinsing, whereas the samples with only salts rinsed off more quickly. This retention effect was quantified by simulating the gel application and rinsing process. The method was set up to capture the retention effect as a function of time. The procedure is illustrated as follows:

1) Mark a 3 inch×2.5 inch area on a glass microscope slide
2) Record weight of microscope slide
3) Place approximately 0.5 g of sample on the slide, spread evenly to cover the marked area, and record weight of slide and sample
4) Fill a 2 oz jar with 50 g deionized water and place a magnetic stir bar at the bottom of the jar
5) Place the slide in the water jar such that the sample area is completely submerged under water and the slide is not touching either walls, bottom of jar, or stir bar.
6) Agitate water in the jar using a magnetic stirrer on at a speed setting four
7) Remove slide from jar at set time intervals (5 minutes, 10 minutes, 30 minutes, 60 minutes, and 2 hours), and remove excess water from slide, but not touching the sample area using Kimwipes
8) Record weight of sample and slide
9) Return sample to water jar to same position as in step (5)
10) Repeat steps (5) to (8) for the remaining time intervals, or until no sample residue is left on slide.

Table 1 below lists results for the samples tested. The samples each contained 16% SLES, 3% CAPB, and 0.0125% of a water soluble blue dye (Acid Blue 9 or Erioglaucine disodium salt); the amount of salt, thickener, and PEG400 were varied; all these compositions were clear isotropic monophasic. Rinse retention was calculated as a percent of the sample remaining on the slide after "rinsing", or submerged in the stirred water, for fixed amounts of time. Although excess water on the slides was dried off before weighing, any water absorbed by the samples was not removed. Hence, some of the percentages can be greater than 100% (e.g. sample 6B).

In all samples where no thickeners were added, the samples mostly rinsed off by 5 minutes of stirring; trace amounts remained on the slides after 10 minutes, and the slides were completely cleaned by 30 minutes. When thickener was used, about half the samples were still retained after 10 minutes of rinsing; significant amounts were still visibly stuck on after 30 minutes, and most samples rinsed off between 1 to 2 hours of soaking and stirring. Comparing 1 and 4% Rewoderm LIS75 levels (although the salt concentrations differed), the higher thickener levels prolonged the retention of the samples during rinsing. Also, PEG400 did not affect the retention trend.

TABLE 1

Compositions and results for gel retention test

| | Composition (16% SLES, 3% CAPB, +) | | | Percent of sample retained on slide as function of "rinsing" time | | | | |
|---|---|---|---|---|---|---|---|---|
| Sample | MgSO4 | Rewoderm LIS75 | PEG400 | 5 minutes | 10 minutes | 30 minutes | 60 minutes | 120 minutes |
| 6A | 4% | 0% | 0% | 28% | 3% | 0% | | |
| 6B | 4% | 4% | 0% | 113% | 102% | 33% | 21% | 3% |
| 6C | 4% | 4% | 11% | 85% | 57% | 18% | 0% | |
| 6D | 4% | 0% | 11% | 43% | 3% | 0% | | |
| 6E | 6% | 0% | 0% | 22% | 5% | 0% | | |
| 6F | 6% | 1% | 0% | 47% | 36% | 14% | 8% | 2% |

What is claimed is:

1. A process for shifting lower the level of salt required to produce or induce dilution thickening effect of a composition, which process comprises adding to said composition 0.5 to 7% by wt. associative thickener;

wherein said composition comprises a single phase, isotropic composition comprising:

(1) 5 to 30% by wt. of a surfactant or surfactants for cleansing the skin wherein said surfactant or surfactants is selected from the group consisting of anionic surfactant, amphoteric surfactant, nonionic surfactant and mixtures thereof;

(2) greater than about 2% to level of electrolyte such that upper limit will not cause isotropic composition to become biphasic or multiphasic;

(3) 0.5 to 7%, by wt. associative thickener;

(4) 0 to 15% by wt., hydrotroping compound; and (5) 45 to 95% by wt. water, wherein, said composition has viscosity upon dilution, which is greater than viscosity prior to dilution;

wherein said composition has rinse retention of greater than 30% by wt. after 10 minutes as measured by a sample retained on a test slide as function of rinsing time;

wherein, upon dilution said composition remains in a single phase; and wherein said process comprises diluting said composition in an amount such that the viscosity of the diluted composition is greater than that of the composition as a neat product (100:0 product to water) up to about a dilution of 25:75 product to water.

2. A process according to claim 1, wherein thickener comprises a polymer with a hydrophobic backbone modified by hydrophobic groups.

* * * * *